US010500588B2

(12) United States Patent
Qin et al.

(10) Patent No.: US 10,500,588 B2
(45) Date of Patent: Dec. 10, 2019

(54) MICROFLUIDIC ALIQUOT CHIP FOR SINGLE-CELL ISOLATION

(71) Applicant: Lidong Qin, Houston, TX (US)

(72) Inventors: Lidong Qin, Houston, TX (US); Kai Zhang, Manvel, TX (US)

(73) Assignee: Lidong Qin, Houston, TX (US)

( * ) Notice: Subject to any disclaimer, the term of this patent is extended or adjusted under 35 U.S.C. 154(b) by 114 days.

(21) Appl. No.: 15/822,071

(22) Filed: Nov. 24, 2017

(65) Prior Publication Data

US 2018/0071736 A1    Mar. 15, 2018

Related U.S. Application Data

(63) Continuation-in-part of application No. 15/701,401, filed on Sep. 11, 2017, now abandoned, which is a continuation of application No. 15/006,634, filed on Jan. 26, 2016, now Pat. No. 9,757,728.

(51) Int. Cl.
*B01L 3/00* (2006.01)
*C12Q 1/04* (2006.01)

(52) U.S. Cl.
CPC ....... *B01L 3/502761* (2013.01); *B01L 3/5027* (2013.01); *C12Q 1/04* (2013.01); *B01L 3/5023* (2013.01); *B01L 2200/0652* (2013.01); *B01L 2200/0668* (2013.01); *B01L 2200/10* (2013.01); *B01L 2300/021* (2013.01); *B01L 2300/0803* (2013.01); *B01L 2300/0806* (2013.01); *B01L 2300/0864* (2013.01); *B01L 2300/0893* (2013.01); *B01L 2300/123* (2013.01); *B01L 2400/0457* (2013.01); *B01L 2400/0487* (2013.01)

(58) Field of Classification Search
CPC ..... B01L 2200/0652; B01L 2200/0668; B01L 2200/10; B01L 2300/021; B01L 2300/0803; B01L 2300/0806; B01L 2300/0864; B01L 2300/0893; B01L 2300/123; B01L 2400/0457; B01L 2400/0487; B01L 3/5023; B01L 3/5027; B01L 3/502761; C12Q 1/04
See application file for complete search history.

(56) References Cited

U.S. PATENT DOCUMENTS

| | | | | |
|---|---|---|---|---|
| 9,164,111 B2 * | 10/2015 | Symonds | ......... | G01N 35/00069 |
| 2005/0019213 A1 * | 1/2005 | Kechagia | ............. | B01L 3/5027 422/504 |
| 2006/0133958 A1 * | 6/2006 | Hsieh | ................ | B01L 3/502723 422/72 |
| 2010/0240051 A1 * | 9/2010 | Wang | ................ | B01L 3/502715 435/6.11 |

* cited by examiner

*Primary Examiner* — Jennifer Wecker
(74) *Attorney, Agent, or Firm* — Michael D. Eisenberg

(57) ABSTRACT

According to the invention, generally, a microfluidic aliquot (MA) chip, adapted to fit in a Petri dish, has a center well (inlet) connected by branched channels to a plurality of side wells (outlets). The chip comes in various types, including a bMA Chip T1, bMA Chip T2, bMA Chip T3, and an rMA Chip. The branched channel improvement provides for a greater distance between neighboring channels and a decreased density near the center well. An insert and a base are configured to create an MA chip.

12 Claims, 17 Drawing Sheets

- 1st Segment
- 2nd Segment
- 3rd Segment

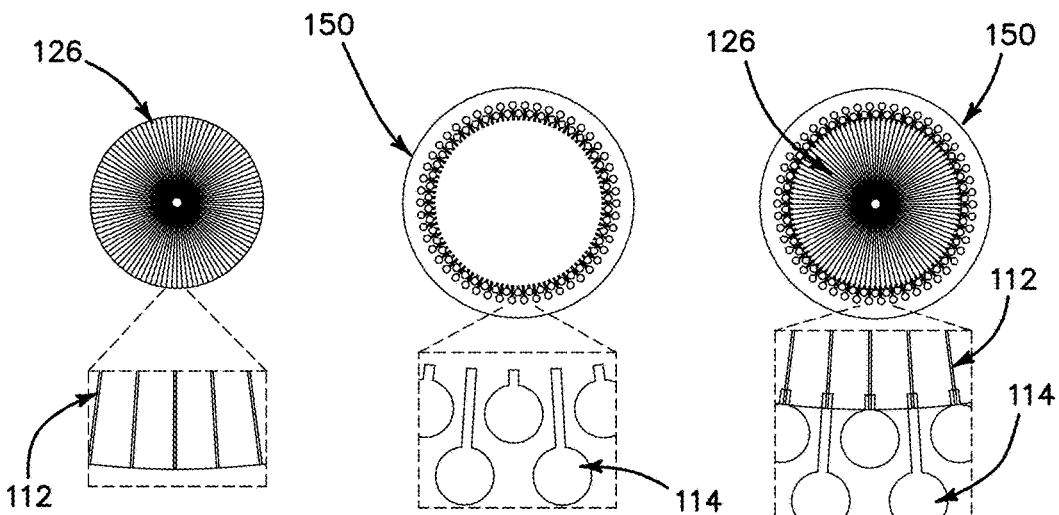
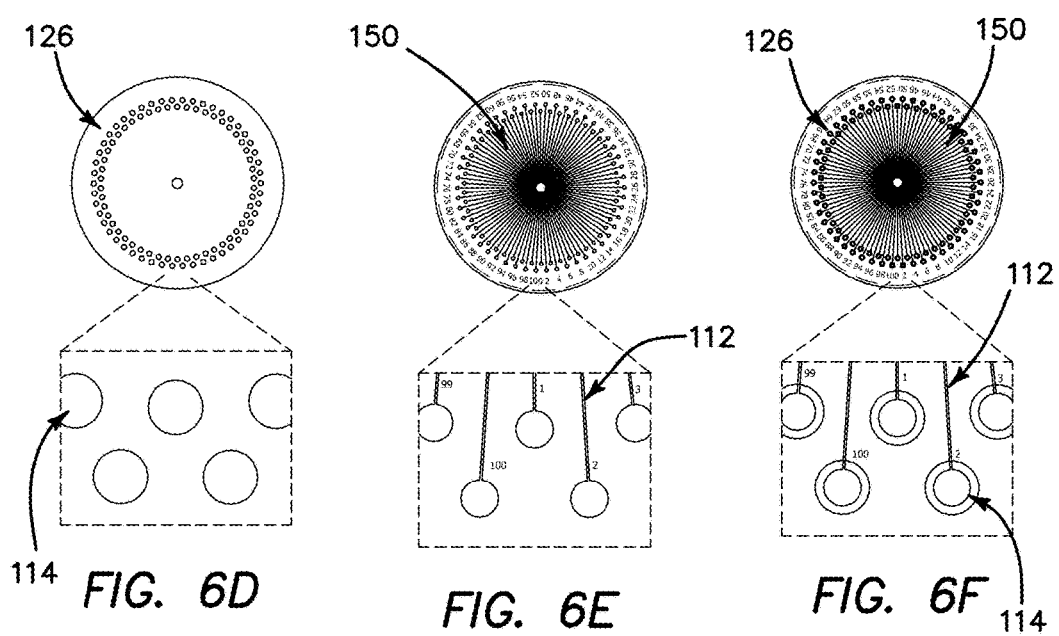

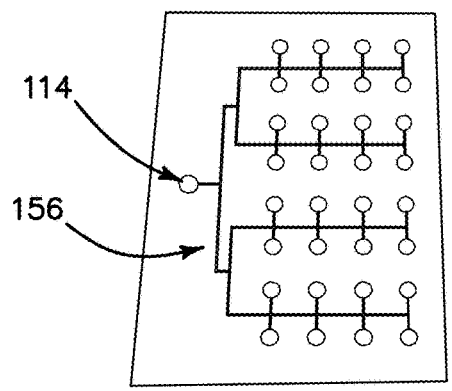
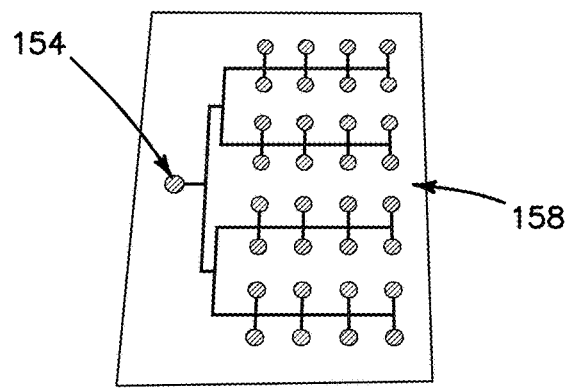
FIG. 9A          FIG. 9B
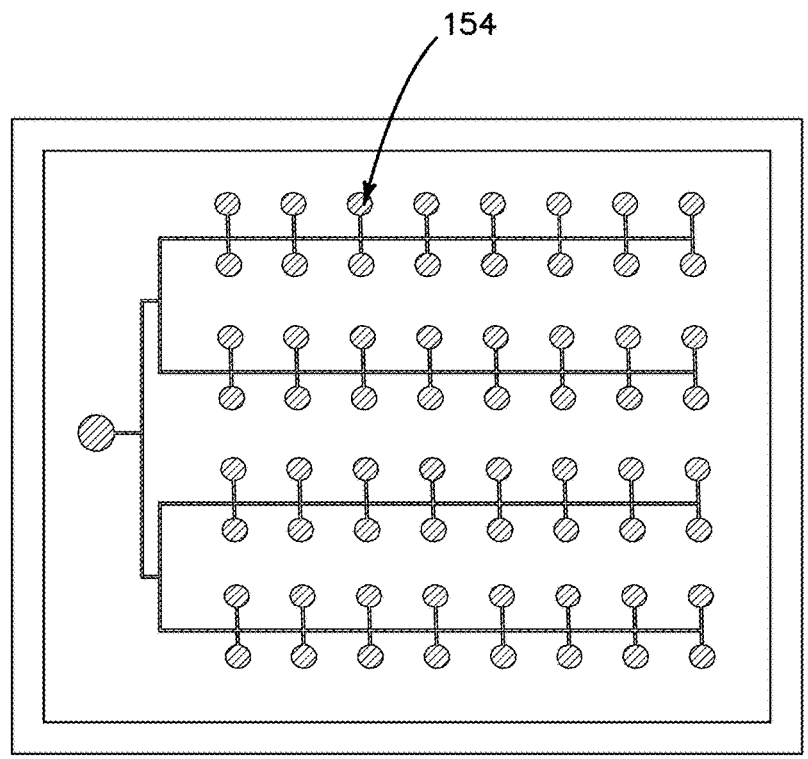
FIG. 9C

MICROFLUIDIC ALIQUOT CHIP FOR SINGLE-CELL ISOLATION

CROSS-REFERENCES TO RELATED APPLICATIONS

The present application is a continuation in part of U.S. application Ser. No. 15/701,401 filed Sep. 11, 2017, which is a continuation of U.S. application Ser. No. 15/006,634 filed Jan. 26, 2016, now issued as U.S. Pat. No. 9,757,728 which are each hereby incorporated herein by reference in their respective entirety.

TECHNICAL FIELD

The present invention, in some embodiments thereof, relates broadly to methods and apparatus for single-cell isolation (such as for processing or analysis) and, more particularly to techniques for isolating single cells using microfluidic technology.

BACKGROUND

Microfluidics is a multidisciplinary field intersecting engineering, physics, chemistry, biochemistry, nanotechnology, and biotechnology, with practical applications to the design of systems in which low volumes of fluids are processed to achieve multiplexing, automation, and high-throughput screening. Advances in microfluidics technology are revolutionizing molecular biology procedures for enzymatic analysis (e.g., glucose and lactate assays), DNA analysis (e.g., polymerase chain reaction and high-throughput sequencing), and proteomics. The basic idea of microfluidic biochips is to integrate assay operations such as detection, as well as sample pre-treatment and sample preparation on one chip.

There is increased evidence that phenotypic and genotypic heterogeneity in cell populations widely exists. The key information from individual rare cells may be masked by bulk cell analysis. Single-cell analysis, especially sequencing of DNA and RNA, has therefore become significantly important for clonal mutation, tumor evolution, embryonic development, and immunological intervention.

The initial and key step for such downstream single-cell genetic analysis is to effectively isolate live single cells of interest from heterogeneous cell populations into submicroliter medium volume, followed by PCR (polymerase chain reaction) analysis. (PCR is a technology in molecular biology used to amplify a single copy or a few copies of a piece of DNA across several orders of magnitude, generating thousands to millions of copies of a particular DNA sequence.)

Besides laser capture microdissection primarily used to isolate single cells from formalin-fixed paraffin-embedded tissue, there are currently four main approaches for single-cell isolation from cell suspensions. The most frequently used method is serial dilution, which has been widely applied for colony formation but is not suited for PCR analysis where single cells should be isolated into submicroliter suspensions for a better amplification reaction. Even so, these colonies are still required for further analysis to judge if they originate from single cells which are very difficult to be accurately counted after seeding into 96-well plates. A second method is micromanipulation, which is mainly developed to isolate single cells for genome/transcriptome sequencing. However, micromanipulation is a time-consuming process and its low throughput feature makes it difficult to rapidly prepare dozens and even hundreds of single cells. Moreover, it is highly dependent on a researcher's ability to suck single cells. Another method is flow cytometry, which is a well-established method particularly suitable for high-throughput sorting of specific cells based on a preset fluorescence gating strategy. However, maintenance of high single-cell viability is challenging and it doesn't work when only a limited number of cells, such as precious clinical samples, are available.

Due to the comparable dimensions of microchannels and cells, microfluidic technology provides a unique and efficient method for single cell manipulation. However, potential disadvantages, including requirement of additional skills for microfluid manipulation, poor compatibility with existing experimental platforms, and inability/difficulty to selectively retrieve the isolated single cells from microchips for further analysis, greatly limit its application in common laboratories. The original Microfluidic Aliquot Chip (MA-Chip) comprises 120 channels that directly connect to one center inlet well in a radial pattern, resulting in a space of less than 40 µm between two neighboring channels around the center inlet well. Although the 40 µm of fabrication resolution can be well achieved by photolithography to make PDMS MA-Chips, it is challenging to fabricate such MA-Chips with plastic materials, such as polystyrene (PS), polypropylene (PP), polycarbonate (PC), and polymethyl methacrylate (PMMA), by using injection molding or laser cutting. Therefore, an alternative design of MA-Chip with the increased space of two neighboring channels is required for the mass fabrication of plastic MA-Chips.

The branched MA-Chip Type 1 (bMA-Chip T1) in the present invention is designed to increase the space between two neighboring channels around the center inlet well while maintaining uniform liquid distribution from the center inlet well to the outlet wells. The original MA-Chip contains one segment, in contrast, the bMA-Chip T1 contains multiple segments, allowing the channel number around the center inlet well to decrease from 120 to 24 and even 12. These improvements reduce channel density and provide an extra space around the center inlet well. As a result, the space between neighboring channels increases from less than 40 µm to more than 400 µm. The improved design in bMA-Chip T1 can meet the requirement for the mass fabrication of plastic MA-Chips.

An objective of the present invention is to provide a technique for simple, rapid, and versatile single-cell isolation using microfluidic technology. In this invention, a single cell is isolated by aliquoting from a suspension of a large number of cells, independently of cell size, shape, and motility. The original microfluidic aliquot chip provides such functions, however it consists of a plurality of straight channels in the chip, resulting in the densely positioned channels. The branched Microfluidic Aliquot Chip-Type 2 (bMA Chip-T2) and the branched Microfluidic Aliquot Chip-Type 3 (bMA Chip-T3) in the present invention are designed as an improvement to the original MA-chip due to the multiple branched channels. This offers the advantage of reduced clogging, strengthened sealing, and enhanced isolation through uniform distribution of flow resistance into the branched channels.

The original design and fabrication methods of the original MA-Chip are based on photolithography followed by soft PDMS casting on the mold. While the photolithography based manufacturing process ensures high resolution of the microstructures in MA-Chip, the daily manufacturing output is limited. The roughly estimated production cycle time for a MA-Chip is 1 hr. This low production rate results in high production costs. To reduce both production costs and final market price, the MA-Chip must be redesigned so that it is appropriate for standard mass production strategy such as the injection molding process. The new design is suitable for a high output production process such as injection molding to greatly increase the production rate.

The injection mold design of the present MA-Chip allows mass production by the injection molding process. With standard operation, the estimated production cycle time for a single device is 10 s, which is 360 times higher than the original rate. Compared to the original design, the new design also improves MA-Chip function, operation, and compatibilities. The device is assembled and packaged for ready to use application. It reduces additional operations such as placing the MA-Chip on a flat sterile surface and ensuring sealing of the flow channel.

The original MA-Chip has a unique design of radial channels connecting a center inlet to surrounding outlet wells and provides the capability to isolate and identify rare single cells in a mixed population with a simple pipetting operation. The vital design and fabrication element is the smooth connection of micrometer scale channels with millimeter scale wells. In the original manufacturing scheme, the micrometer size channels (30-80 μm) are fabricated by soft lithography followed by PDMS molding, and the millimeter scale wells (1.5-2 mm) are created by mechanical punch press. Thus, this manual operation demands a significant amount of time and labor. To improve throughput of the hole punch process, a multiplexed hole punch device is designed.

A multiplex hole punch strategy for the rapid fabrication of MA-Chip is designed to meet the requirement of mass production while maintaining the original MA-Chip manufacturing format. Current operation requires the holes to be punched manually by trained individuals. In one MA-Chip, there are 96-120 holes and alignment is required in each hole punch process. The quality of outcome and labor time in this process highly depends on the operator's skill and experience. The multiplex hole punch is designed to increase throughput of the hole punch process while maintaining the original design format of the MA-Chip.

Photolithography is suitable for fabricating high quality PDMS channels but difficult for making holes. In contrast, laser cutting or injection molding can easily achieve mass production of plastic holes but difficult to make high quality channels. The two methods can be combined to achieve rapid fabrication of MA-Chips. The present invention includes a basic strategy for the rapid fabrication of MA-Chip to meet the requirement of mass production. The operation is to align and combine two patterned layers.

In the original MA-Chip, the outlet wells are primarily located in the edge of the device with a radial pattern. However, the majority of the MA-Chip is occupied by radial channels, resulting in wasted space and difficulty in further increasing the number of outlet wells to meet the requirement of high-throughput assay, such as a device containing hundreds to thousands of wells. Therefore, a new design of the MA-Chip is required. The present invention has a rectangular MA-Chip (rMA-Chip) that has the potential to integrate hundreds to thousands of outlet wells in the size of a standard 96-well plate.

U.S. Pat. No. 6,632,656 (Oct. 14, 2003; Thomas et al.), incorporated by reference herein, discloses apparatus and methods for performing cell growth and cell based assays in a liquid medium. The apparatus comprises a base plate supporting a plurality of micro-channel elements, each micro-channel element comprising a cell growth chamber, an inlet channel for supplying liquid sample thereto and an outlet channel for removal of liquid sample therefrom, a cover plate positioned over the base plate to define the chambers and connecting channels, the cover plate being supplied with holes to provide access to the channels. Means are incorporated in the cell growth chambers, for cell attachment and cell growth. More particularly, as shown and described therein:

Referring to FIG. 1b, the apparatus comprises a rotatable disc (18) microfabricated to provide a sample introduction port located towards the centre of the disc and connected to an annular sample reservoir (9) which in turn is connected to a plurality of radially dispersed micro-channel assay elements (6) each of said micro-channel elements comprising a cell growth chamber, a sample inlet channel and an outlet channel for removal of liquid therefrom and a cover plate positioned onto said disc so as to define closed chambers and connecting channels. Each micro-channel element is connected at one end to the central sample reservoir (9) and at the opposing end to a common waste channel (10).

Each of the radially-dispersed micro-channel elements (6) of the microfabricated apparatus (shown in FIG. 1a) comprises a sample inlet channel (1) connected at its left hand-end end to the reservoir (9), a cell growth chamber (2) for performing cell growth and connected through a channel (4) to an assay chamber (3) and an outlet channel (5) connected at its right-hand end to the waste channel (10).

Suitably the disc (18) is of a one- or two-piece moulded construction and is formed of an optionally transparent plastic or polymeric material by means of separate mouldings which are assembled together to provide a closed structure with openings at defined positions to allow loading of the device with liquids and removal of waste liquids. In the simplest form, the device is produced as two complementary parts, one or each carrying moulded structures which, when affixed together, form a series of interconnected micro-channel elements within the body of a solid disc. Alternatively the micro-channel elements may be formed by micro-machining methods in which the micro-channels and chambers forming the micro-channel elements are micro-machined into the surface of a disc, and a cover plate, for example a plastic film, is adhered to the surface so as to enclose the channels and chambers.

The scale of the device will to a certain extent be dictated by its use, that is the device will be of a size which is compatible with use with eukaryotic cells. This will impose a lower limit on any channel designed to allow movement of cells and will determine the size of cell containment or growth areas according to the number of cells present in each assay. An average mammalian cell growing as an adherent culture has an area of ~300 $\mu m^2$; non-adherent cells and non-attached adherent cells have a spherical diameter of ~10 μm. Consequently channels for movement of cells within the device are likely to have dimensions of the order of 20-30 μm or greater. Sizes of cell holding areas will depend on the number of cells required to carry out an assay (the number being determined both by sensitivity and statistical requirements). It is envisaged that a typical assay would require a minimum of 500-1000 cells which for adherent cells would require structures of 150,000-300,000 $\mu m^2$, i.e. circular 'wells' of ~400-600 μm diameter.

The configuration of the micro-channels . . . is preferably chosen to allow simultaneous seeding of the cell growth chamber by application of a suspension of cells in a fluid medium to the sample reservoir by means of the sample inlet port, followed by rotation of the disc (18) by suitable means at a speed sufficient to cause movement of the cell suspension outward towards the periphery of the disc by centrifugal force. The movement of liquid distributes the cell suspension along each of the inlet micro-channels (1, 8) towards the cell growth chambers (2, 7). The rotation speed of the disc is chosen provide sufficient centrifugal force to allow liquid to flow to fill the cell growth chamber (2, 7), but with insufficient force for liquid to enter the restricted channel (4, 16) of smaller diameter on the opposing side of the cell growth chamber.

BRIEF SUMMARY OF THE EMBODIMENTS OF THE INVENTION

In a variant, a microfluidic aliquot (MA) chip for isolating cells, comprises a chip having a center, a top surface, a bottom surface, an outer edge and a thickness. The chip has an inlet well disposed substantially at the center of the chip, extending into and accessible from the top surface of the chip. A plurality of outlet wells are disposed in an outer portion of the chip, extending into and accessible from the top surface of the chip. A plurality of multiple segments extend from the inlet well to the outlet wells, wherein the multiple segments comprise branched channels. The chip is configured to maintain uniform distribution of a liquid and cells from the inlet well to the outlet wells.

In another variant, the MA chip comprises a plurality of first segments that form an inner section, a plurality of last segments that form an outer section, and a plurality of segments between the first segments and the last segments that form a middle section. The first segment is connected to the center inlet well in a radial pattern and each segment after the first segment is divided from a prior segment in a radial pattern. A first channel of a last segment is shorter than a second channel of the last segment. Every other outlet well is disposed farther away from the inlet well than an adjacent outlet well.

In a further variant, the plurality of segments in the middle section form a curved portion generally in the shape of a bend, whereby one of the first segments is joined to the bend of a segment in the middle section.

In yet another variant, the chip comprises four first segments that extend outward from the inlet well in four cardinal directions, respectively. Each segment branches at a 90 degree angle in two opposite directions into another segment forming a set of branched channels. Each set of branched channels on a last segment correspond to a set of outlet wells.

In another variant, the chip comprises a plurality of first segments that extend outward radially from the inlet well. Each segment branches at a 90 degree angle in two opposite directions into another segment forming a set of branched channels. Each set of branched channels on a last segment correspond to a set of outlet wells.

In a further variant, the chip comprises a sheet of material selected from a group consisting of polydimethylsiloxane (PDMS), PMMA (poly(methyl methacrylate)), PS (polystyrene), and PC (polycarbonate). The sheet has a top surface and a bottom surface, that correspond to the top and bottom surfaces of the chip, respectively.

In yet another variant, the chip comprises a center inlet well having a diameter of 2-4 mm and a volume of 3-5 µl. A plurality of side outlet wells have a diameter of 1.5-2 mm and a volume of 1-3 µl. A plurality of branched channels have a width of 50-100 µm. The chip is configured to fit within a Petri dish of 8.5-10 cm.

In another variant, the chip comprises a first layer having a top surface and a bottom surface and a second membrane layer having a top surface and a bottom surface. The bottom surface of the second membrane layer has an adhesive and the bottom surface of the second membrane layer is configured to adhere to the top surface of the first layer.

In a further variant, the top surface of the first layer comprises an inlet well, an outlet well array, a main-channel array, and a sub-channel array. The main channels are longer and wider than the sub-channels. The main channels extend outward from the inlet well to the sub-channels and the sub-channels extend from the main channels to the outlet wells.

In yet another variant, the chip comprises a second membrane layer that has a thickness of 0.03-0.3 mm. A plurality of outlet wells have a diameter of 0.5-5 mm and a height of 1-10 mm. The chip has a length of 127.8±5 mm, a width of 85.5±3 mm, and a height of 1-10 mm.

In another variant, the inlet well comprises a cap having a hole that is configured to attach onto the inlet well and receive a cell suspension.

In a further variant, the center inlet well is configured to receive and distribute liquid through the branched channels and into the outlet wells.

In yet another variant, an MA chip insert for making an MA chip, comprises a center through-hole, a plurality of aliquoting through-holes, a plurality of branched channels, a plurality of outlet wells, a bottom surface, a top surface, a flattened edge, and a plurality of rivet through-holes. The insert has a design configured to match a design of an MA chip.

In another variant, an MA chip base for making an MA chip, comprises a bottom surface having bottom pillars, a top surface having edge wells, a sink plateau surface having a flattened edge, and a plurality of rivets.

In a further variant, a method for making an MA chip, comprises inserting a first pair of patterned metal injection molds into an injection molding machine; injecting thermoplastic into the first pair of patterned metal injection molds; demolding to produce an insert having a reverse pattern of the first pair of molds; inserting a second pair of patterned metal injection molds into the injection molding machine; inserting thermoplastic into the second pair of patterned metal injection molds; demolding to produce a base having a reverse pattern of the second pair of molds; inserting a plurality of rivets on the base into a plurality of rivet through-holes on the insert; and sealing a center through-hole, branched channels, and aliquoting through-holes disposed on the insert when the rivets are inserted into the rivet through-holes.

In yet another variant, a method for creating holes in an MA chip, comprises inserting an MA chip between a top and a bottom of an enclosure; aligning the MA chip directly above a reverse mold in the enclosure; inserting a plurality of pins attached to a bottom of a pin head into a plurality of tapered holes on the top of the enclosure; and pressing a top of the pin head so that the MA chip is pushed into the reverse mold. The MA chip and enclosure are aligned when the reverse mold has a pattern that matches a pattern on the MA chip and the reverse mold has a flattened edge that matches a flattened edge on the enclosure.

In another variant, a method for mass production of MA chips, comprises conducting photolithography to produce a silicon mold; injecting Polydimethylsiloxane (PDMS) into the silicon mold; heating the silicon mold containing the PDMS to produce a first layer of an MA chip having channels and an inlet well; cutting plastic material with a laser to produce a second layer of an MA chip having a well array and channels; and aligning the first layer directly on top of the second layer so the channels on both layers overlap. The channels on the first layer are longer and narrower than the channels on the second layer.

In a further variant, a method for mass production of MA chips, comprises cutting plastic material with a laser to produce a first layer of an MA chip having a well array and an inlet well; conducting photolithography to produce a silicon mold; injecting Polydimethylsiloxane (PDMS) into the silicon mold; heating the silicon mold containing the PDMS to produce a second layer of an MA chip having radial channels and an alignment mark array; and aligning the first layer directly on top of the second layer so the well array and the alignment mark array overlap.

In yet another variant, a method for making MA chips, comprises cutting plastic material with a laser to produce a first layer of an MA chip having an inlet well, outlet well array, main-channel array, and sub-channel array; adhering a second membrane layer on top of the first layer using an adhesive on the second membrane layer; cutting an area of the membrane directly on top of the inlet well with a puncher; and securing a PDMS cap on top of the exposed inlet well. The cap is configured to receive liquid, which distributes from the cap to the inlet well, the main channels, the sub-channels, and finally the outlet wells.

BRIEF DESCRIPTION OF THE DRAWINGS

FIG. 6A is an MA chip assembly with long and narrow channels on a top layer.
FIG. 6B is an MA chip assembly with short and wide channels on a bottom layer.
FIG. 6C is an MA chip assembly with the top and bottom layer combined.
FIG. 6D is an MA chip assembly with short and wide channels on a top layer.
FIG. 6E is an MA chip assembly with long and narrow channels on a bottom layer.
FIG. 6F is an MA chip assembly with the top and bottom layer combined.
FIG. 9A is an rMA chip before loading liquid into the chip.
FIG. 9B is an rMA chip after loading liquid into the chip.
FIG. 9C is an rMA chip after removing the tape.

DETAILED DESCRIPTION

Figure 1A:
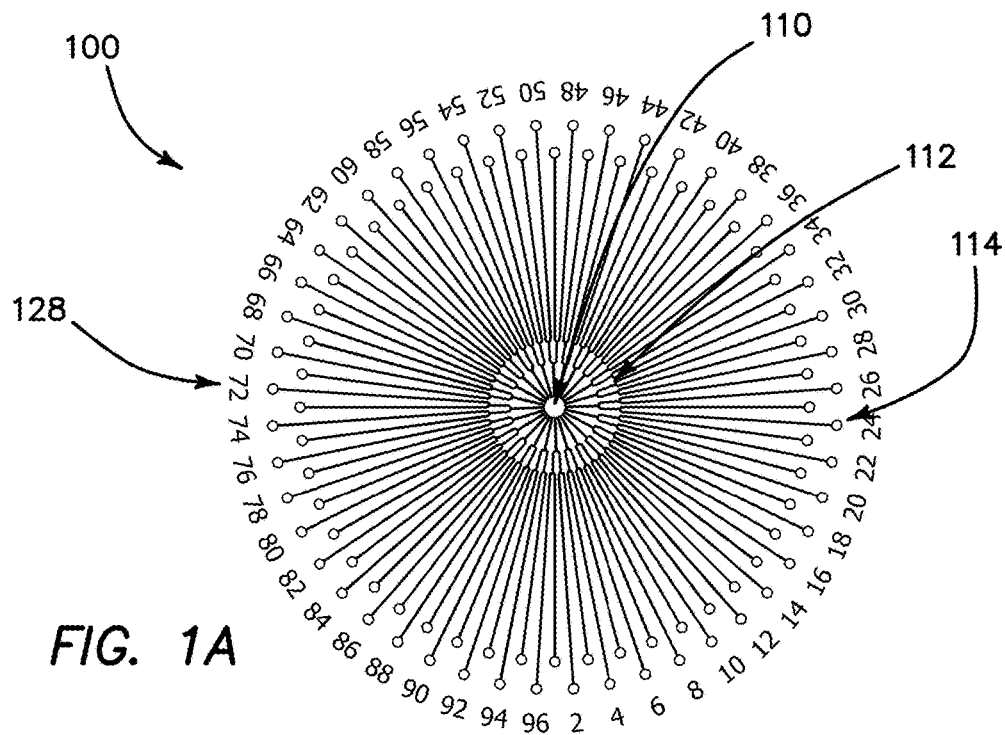
FIG. 1A is a bMA Chip Type 1.

The following Reference Numbers are used in this document:
100 Microfluidic Aliquoting (MA) chip
110 Inlet well
112 Plurality of channels
114 Plurality of outlet wells
114a First segments
114b Second segments
114c Third segments
114d Fourth segments
116 Width of first segments
118 Width of second segments
122 Width of third segments
126 Top surface of MA chip
128 Identifying millimeter-scale number
129 Sealed flow channel
130 MA Chip Base
131 Aliquoting through-holes
132 Liquid reservoir wells
133 Open flow channel
134 Joining rivet
135 Plurality of rivet through-holes
136 Engraved identification number
137 Center through-hole
138 Flattened edge
139 Insert
140 Multiplex hole punch pin head
141 Sink Plateau surface
142 Top enclosure of multiplex hole punch
143 Pins
144 Reverse mold of MA chip
146 Bottom enclosure of multiplex hole punch
148 MA chip with microchannel array
150 Bottom surface of MA chip
152 Impermeable membrane
154 Well filled with liquid
156 rMA Chip
158 rMA Chip with liquid
160 384 well rMA Chip Section 1: Branched Microfluidic Aliquot Chip Type 1 (bMA-Chip T1)

Figure 1B:
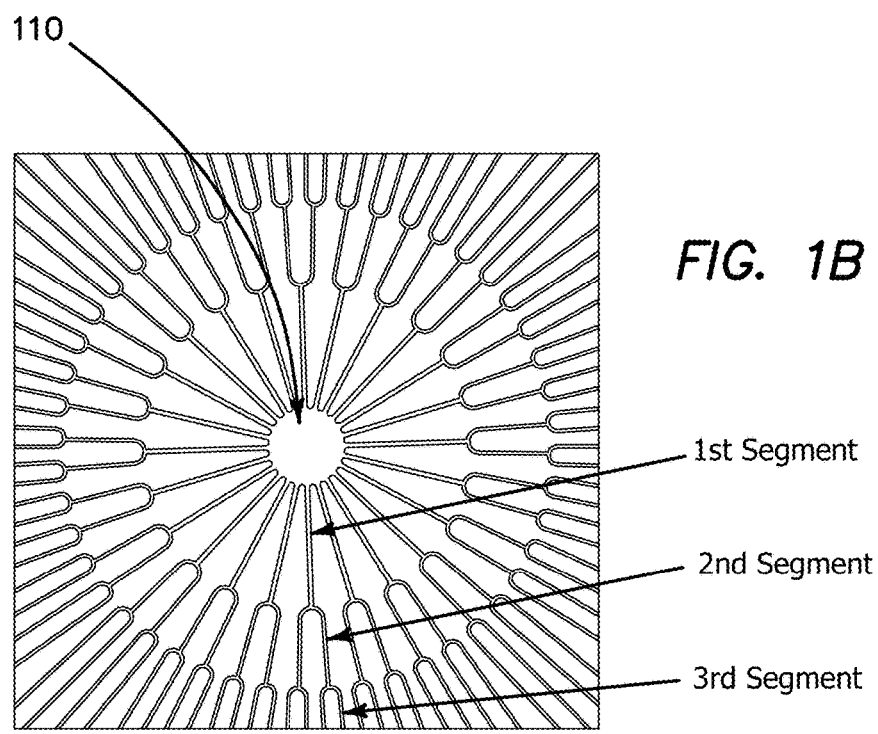
FIG. 1B is a magnified portion of the MA chip in FIG. 1A.
Figure 1C:
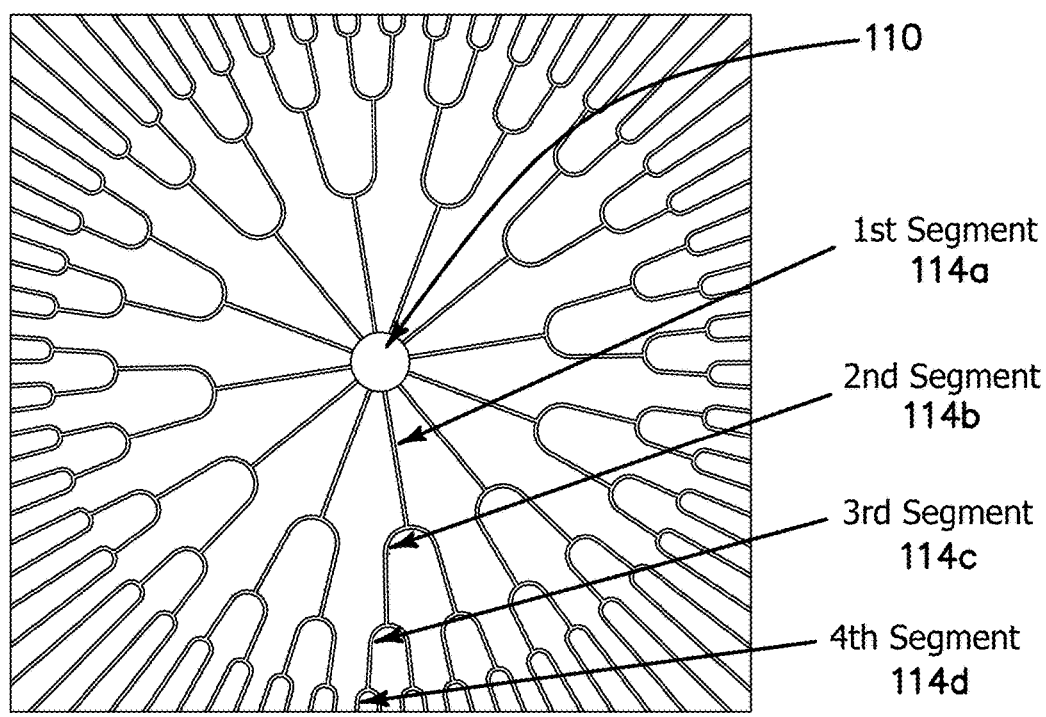
FIG. 1C is a magnified portion of an MA chip with four segments.
Figure 2A:
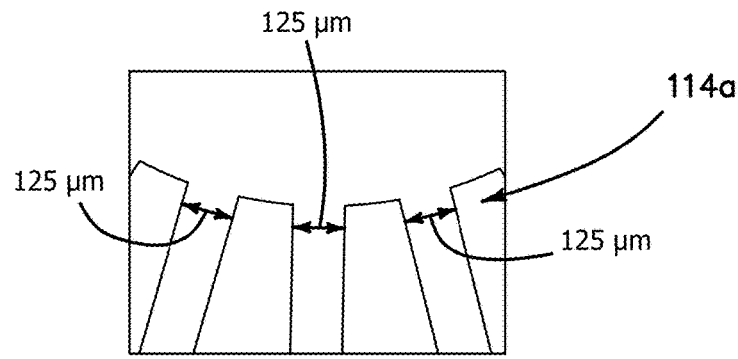
FIG. 2A is a magnified portion of a first segment of an MA chip.
Figure 2B:
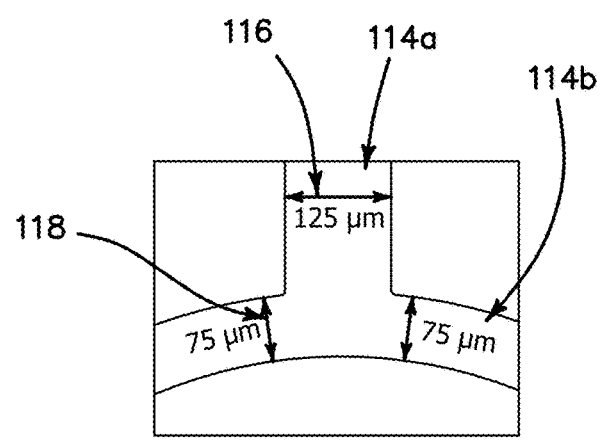
FIG. 2B is a magnified portion of a second segment of an MA chip.
Figure 2C:
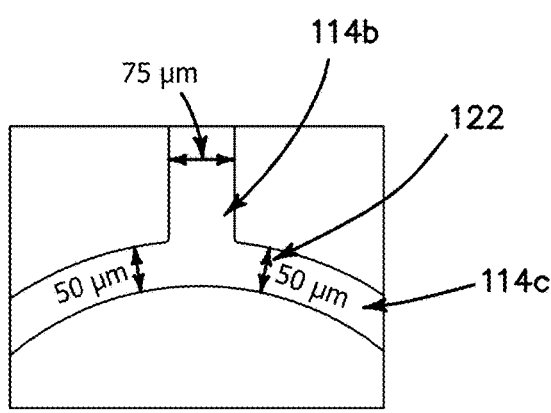
FIG. 2C is a magnified portion of a third segment of an MA chip.
Figure 2D:
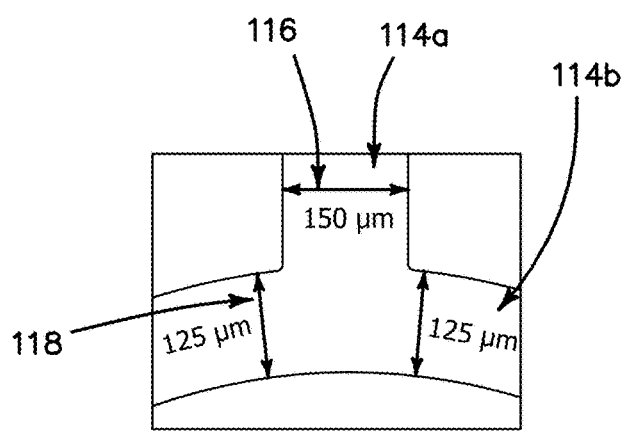
FIG. 2D is a magnified portion of a second segment of an MA chip.

In a variant, referring generally to FIGS. 1A-1C, the bMA-Chip Type 1 comprises a chip 100 having a center, a top surface 126, a bottom surface 150, an outer edge and a thickness. The chip 100 has an inlet well 110 disposed substantially at the center of the chip 100, extending into and accessible from the top surface 126 of the chip 100. A plurality of outlet wells 114 are disposed in an outer portion of the chip 100, extending into and accessible from the top surface 126 of the chip 100. A plurality of multiple segments 112 extend from the inlet well 110 to the outlet wells 114, wherein the multiple segments 112 comprise branched channels. A plurality of first segments 114a form an inner section, a plurality of last segments form an outer section, and a plurality of segments between the first segments and the last segments form a middle section. The first segment 114a is connected to the inlet well 110 in a radial pattern and each segment after the first segment 114a is divided from a prior segment in a radial pattern. The plurality of segments in the middle section form a curved portion generally in the shape of a bend, whereby one of the first segments 114a is joined to the bend of a segment in the middle section. A first channel of a last segment is shorter than a second channel of the last segment. Every other outlet well 114 is disposed farther away from the inlet well 110 than an adjacent outlet well 114.

In another variant, the multiple segments 112 connect the inlet well 110 to 96 outlet wells 114. The number of channels in each segment, from the inside section to the outside section, is 24, 48, and 96, respectively. The bMA-Chip T1 can also contain four segments: the 1st segment 114a (inside section), the 2nd 114b and 3rd segments 114c (middle sections), and the 4th segment 114d (outside section). The number of channels in each segment, from the inside section to the outside section, is 12, 24, 48, and 96 channels, respectively. The bMA-Chip T1 can also contain other segments, such as 2, 5, and 6. The liquid and cells can be uniformly distributed into 96 outlet wells 114 through the multiple segments 112 of bMA-Chip T1. The chip 100 is configured to maintain uniform distribution of a liquid and cells from the inlet well to the outlet wells.

Referring generally to FIGS. 2A-2D, in a further variant, the distance between the segments vary. The first segments 114a have a width 116 of 125 µm. The second segments 114b have a width 118 of 75 µm. The third segments 114c have a width 122 of 50 µm. When there are 4 segments, the first segments 114a have a width 116 of 150 µm, second segments 114b have a width 118 of 125 µm, third segments 114c have a width 122 of 75 µm, and fourth segments 114d have a width of 50 µm.

Section 2: Branched Microfluidic Aliquot Chip Type 2 (bMA-Chip T2)

Figure 3A:
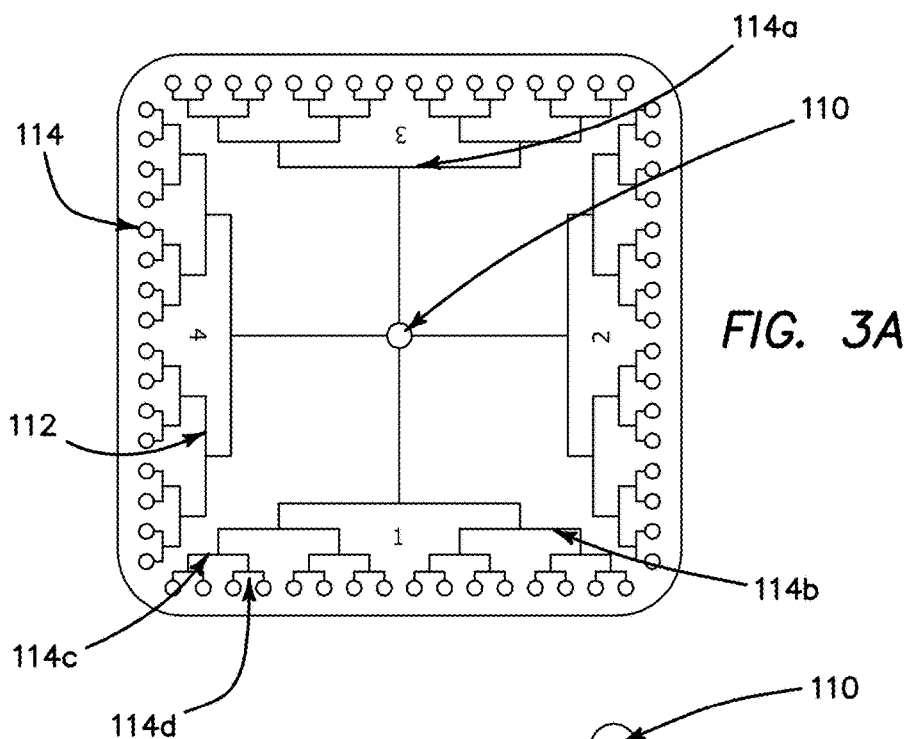
FIG. 3A is a diagram of a bMA Chip Type 2.
Figure 3B:
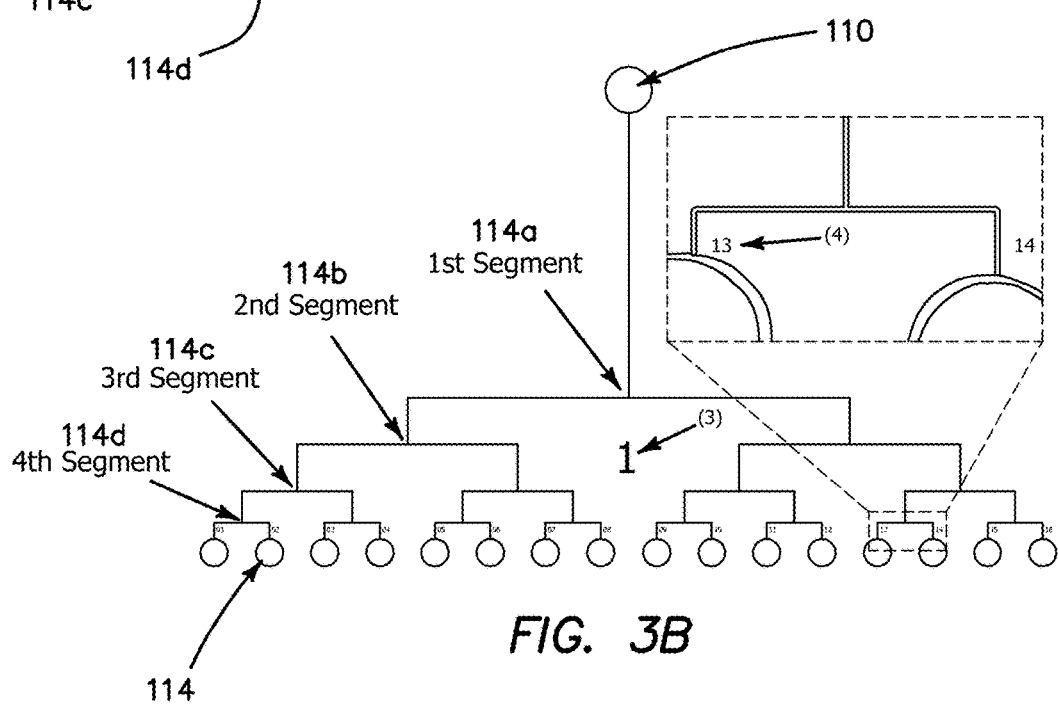
FIG. 3B is a magnified portion of a bMA Chip Type 2.

In a variant, referring to FIGS. 3A-3B, the bMA Chip-T2 comprises four first segments 114a that extend outward from the inlet well 110 in four cardinal directions, respectively. Each segment branches at a 90 degree angle in two opposite directions into another segment forming a set of branched channels. Each set of branched channels on a last segment correspond to a set of outlet wells 114. The chip also comprises a thin sheet of flexible or semi-rigid material such as, polydimethylsiloxane (PDMS), PS (polystyrene) PC (polycarbonate), and PMMA (poly (methyl methacrylate)) with a thickness of approximately 1 mm. The bMA Chip-T2 has the overall form of a square, having a geometric center and a side of approximately 6 cm. The bMA Chip-T2 is sized and shaped to fit in a Petri dish having a diameter of approximately 8.5-10 cm. The sheet forming the bMA Chip-T2 has a top surface and a bottom surface, corresponding to the top 126 and bottom 150 surfaces of the overall bMA Chip-T2, respectively. The inlet well has a diameter of approximately 2-4 mm. The inlet well has a volume of 3-5 µl. The inlet well is disposed at the geometric center of the bMA Chip-T2. The inlet well is accessible to a user from the top surface 126 of the bMA Chip-T2, for loading a cell suspension into the bMA Chip-T2.

In another variant, the outlet wells 114 are in the form of round holes extending completely through the bMA Chip-T2. The outlet wells 114 may be in the shape of an oval, triangle, square, rectangle, rhombus, trapezoid, or pentagon. The outlet wells 114 have a diameter of 1.5-2 mm. The outlet wells 114 each have a volume of 1-3 µl. The outlet wells 114 are distributed along four cardinal directions of the bMA Chip-T2. The outlet wells 114 are accessible to a user from the top surface 126 of the bMA Chip-T2, for retrieving isolated cells from the bMA Chip-T2.

In a further variant, 16 outlet wells 114 are arranged into a set of branched channels, corresponding to a total of 64 outlet wells 114 arranged into four sets of branched channels. All channels have a width of approximately 50 µm. Each set of branched channels consists of four segments that are connected to 16 outlet wells 114. The total number of branched channels in each set from the 1st segment 114a to the 4th segment 114d is 2, 4, 8, and 16, respectively. Relatively small µm-scale markings are disposed inside the outlet wells 114 for identifying the outlet wells 114 under microscopic observation, and relatively large mm-scale markings 128 are disposed outside of the 1st segment 114a along four cardinal directions.

Section 3: Branched Microfluidic Aliquot Chip Type 3 (bMA-Chip T3)

Figure 3C:
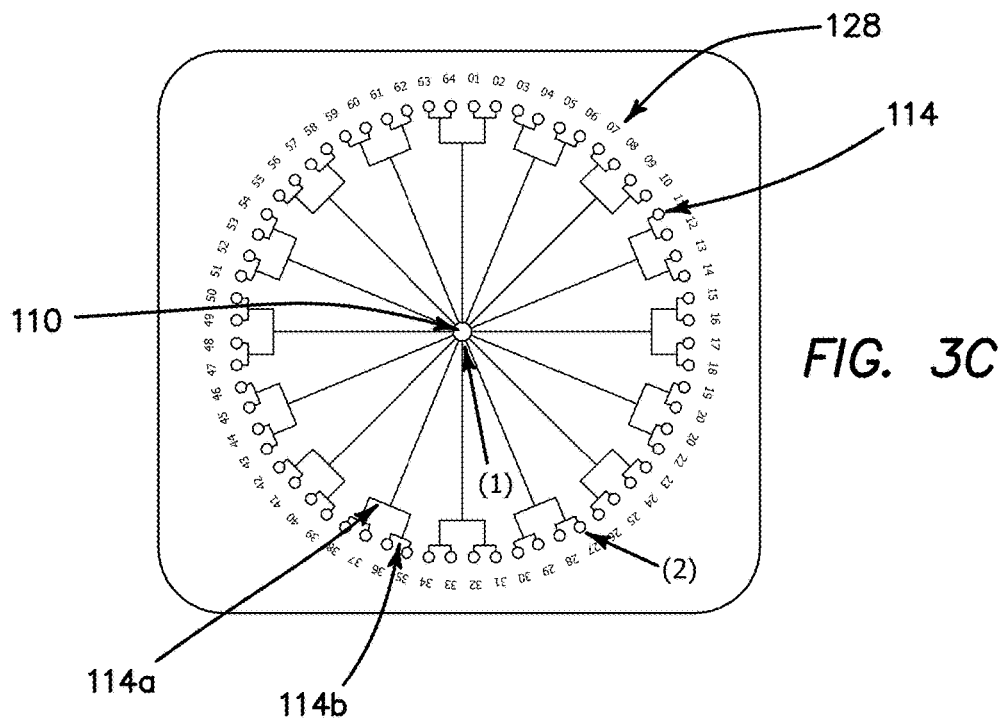
FIG. 3C is a bMA Chip Type 3.
Figure 3D:
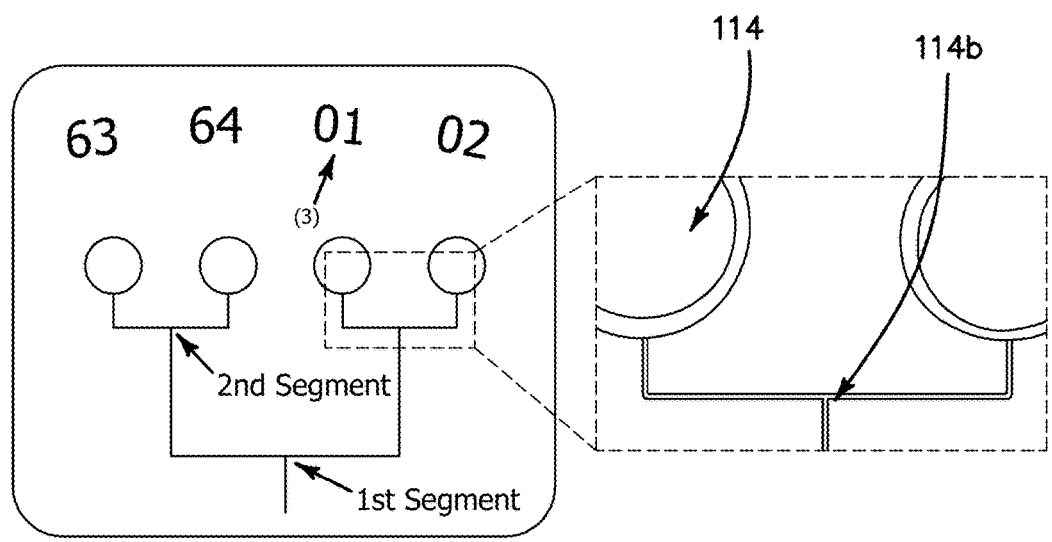
FIG. 3D is a magnified portion of a bMA Chip Type 3.

In a variant, referring to FIGS. 3C-3D, the bMA Chip-T3 comprises a plurality of first segments 114a that extend outward radially from the inlet well 110. Each segment branches at a 90 degree angle in two opposite directions into another segment forming a set of branched channels. Each set of branched channels on a last segment correspond to a set of outlet wells 114. The chip further comprises a thin sheet of flexible or semi-rigid material such as, polydimethylsiloxane (PDMS), PS (polystyrene) PC (polycarbonate), and PMMA (poly (methyl methacrylate)) with a thickness of approximately 1 mm. The bMA Chip-T3 has the overall form of a disk, having a geometric center and a diameter of approximately 8 cm. The bMA Chip-T3 is sized and shaped to fit in a Petri dish having a diameter of approximately 8.5-10 cm. The sheet forming the bMA Chip-T3 has a top surface and a bottom surface, corresponding to the top 126 and bottom 150 surfaces of the overall bMA Chip-T3, respectively.

In another variant, the inlet well 110 has a diameter of approximately 2-4 mm and a volume of 3-5 µl. The inlet well 110 is disposed at the geometric center of the bMA Chip-T3 and is accessible to a user from the top surface of the bMA Chip-T3, for loading a cell suspension into the bMA Chip-T3. The outlet wells 114 are in the form of round holes extending completely through the bMA Chip-T3. The outlet wells 114 may be in the shape of an oval, triangle, square, rectangle, rhombus, trapezoid, or pentagon. The outlet wells 114 have a diameter of approximately 1.5-2 mm and a volume of 1-3 µl. The outlet wells 114 are distributed around an outer annular portion of the bMA Chip-T3 with the branched channels. The outlet wells 114 are accessible to a user from the top surface of the bMA Chip-T3, for retrieving isolated cells from the bMA Chip-T3.

In a further variant, four outlet wells 114 are arranged into a set of branched channels, corresponding to a total of 64 outlet wells 114 arranged into 16 sets of branched channels. All channels have a width of approximately 50 μm. Each set of branched channels consists of two segments that are connected to 4 total outlet wells 114. The total number of branched channels for the 1st segment 114a and the 2nd segment 114b is 32 and 64, respectively.

In yet another variant, relatively large mm-scale markings 128 are disposed outside of the outlet wells 114 for identifying the outlet wells 114 under naked-eye observation. The markings 128 may be other than numbers or letters, such as 1D and 2D barcodes for identifying the outlet wells 114 by using an imaging software. For the linear 1D barcodes, the information is stored in the relationship of the widths of the bars (spaces) to each other. For the stacked 2D barcodes, several stacked linear barcodes are used to encode the information. Compared to stacked barcodes the information of the matrix 2D barcodes is not stored by using different bar (space) widths. Instead the position of black or white dots is relevant.

Section 4: Injection Mold Design

Figure 4A:
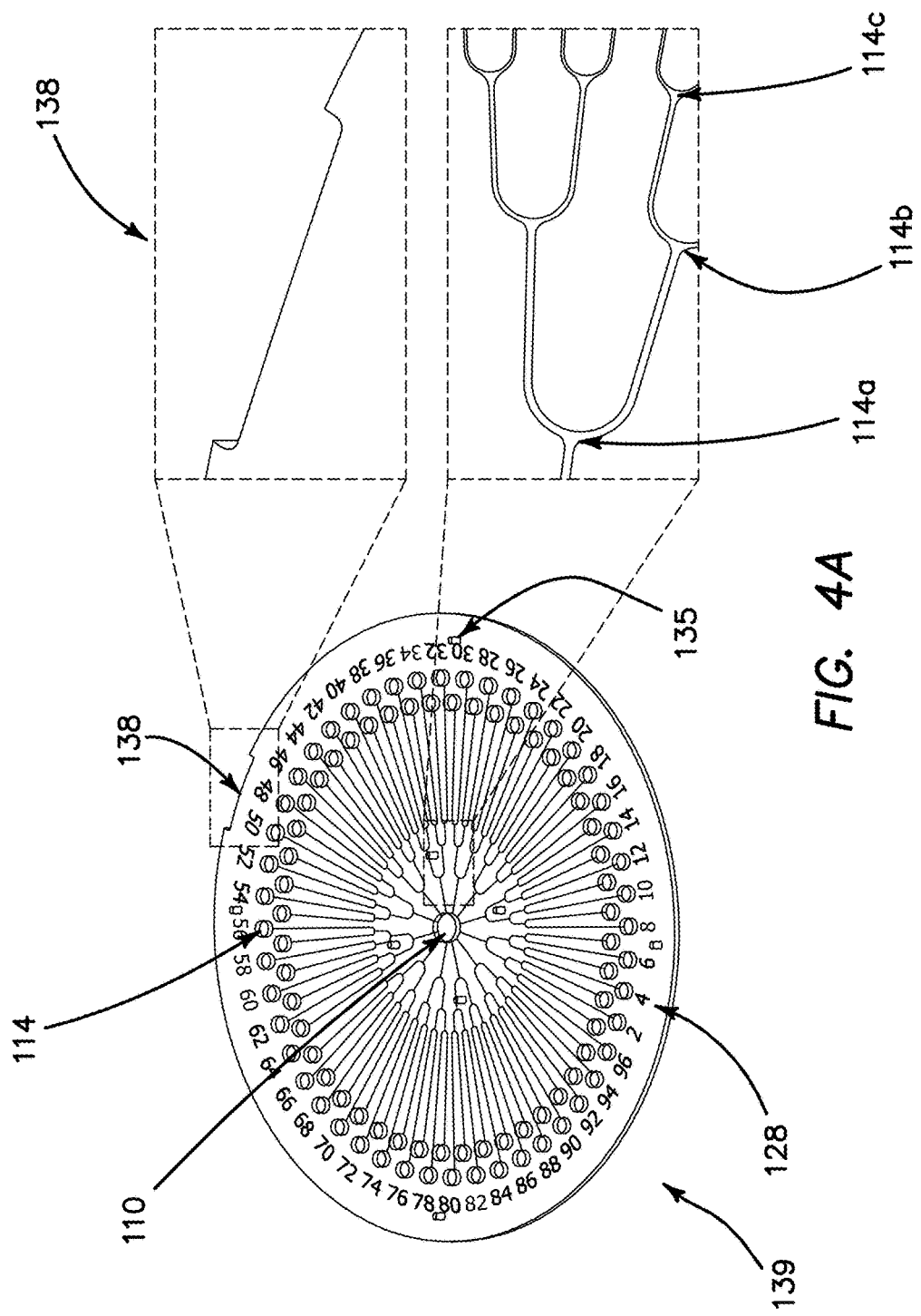
FIG. 4A is an MA chip insert.

In a variant, referring to FIG. 4A, an MA chip insert 139 for making an MA chip 100, comprises a center through-hole 137, a plurality of aliquoting through-holes 131, a plurality of branched channels, a plurality of outlet wells 114, a bottom surface, a top surface, a flattened edge 138, and a plurality of rivet through-holes 135. The insert 139 has a design configured to match a design of an MA chip 100. The rivet through-holes 135 are placed in a pattern on the insert 139 illustrated in FIG. 4A, and correspond in spacing to corresponding rivets 134 on the base 130 in FIG. 4B.

Figure 4B:
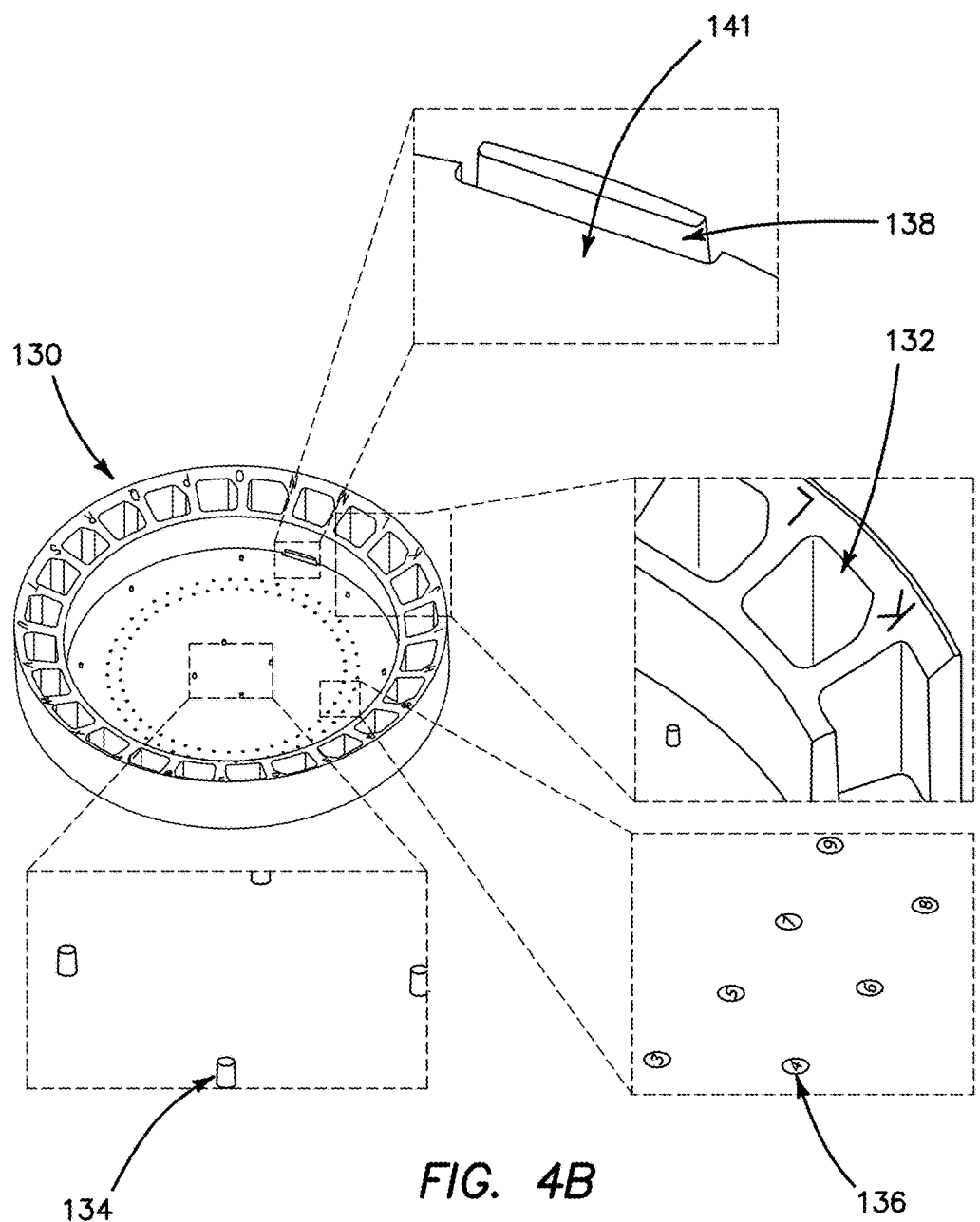
FIG. 4B is an MA chip base.

In another variant, referring to FIG. 4B, an MA chip base 130 for making an MA chip 100, comprises a bottom surface having bottom pillars, a top surface having edge wells, a sink plateau surface 141 having a flattened edge 138, and a plurality of rivets 134.

Figure 4C:
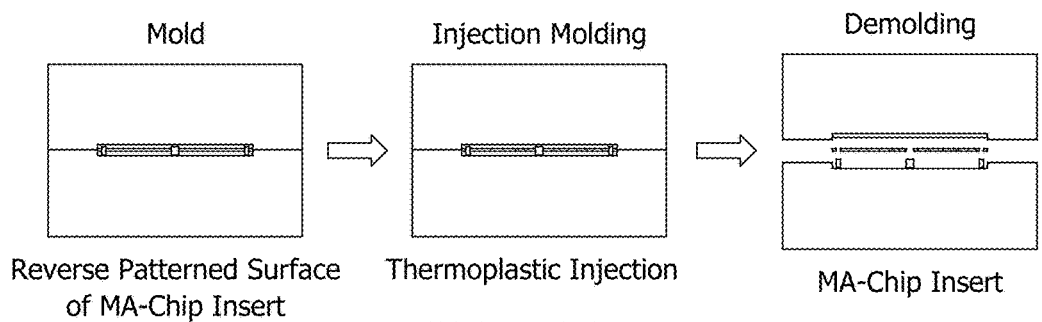
FIG. 4C is a method for making an MA chip insert.
Figure 4D:
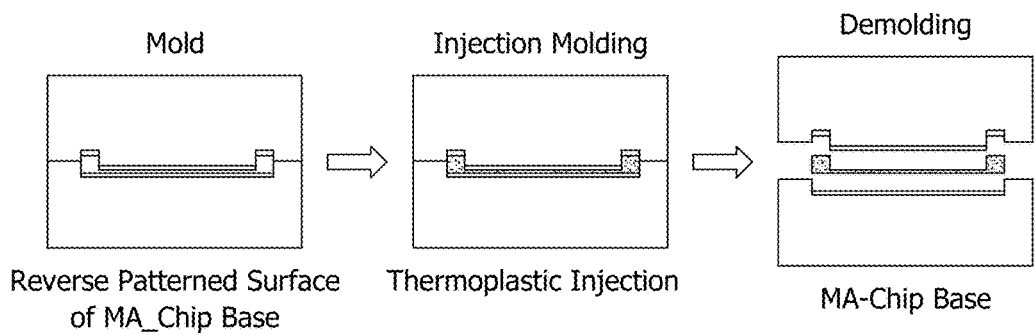
FIG. 4D is a method for making an MA chip base.
Figure 4E:
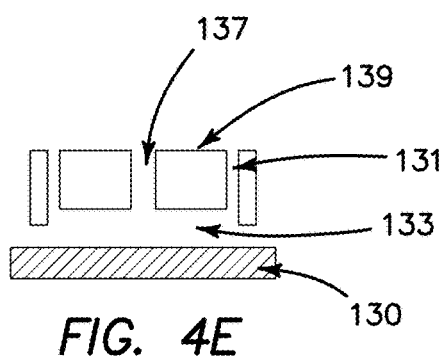
FIG. 4E is the insert and base prior to being assembled together.
Figure 4F:
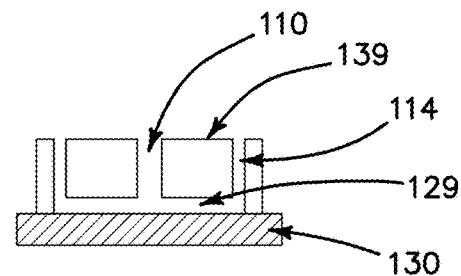
FIG. 4F is the insert and base after the process of assembling them together as described in the methods of FIGS. 4C and 4D.
Figure 5:
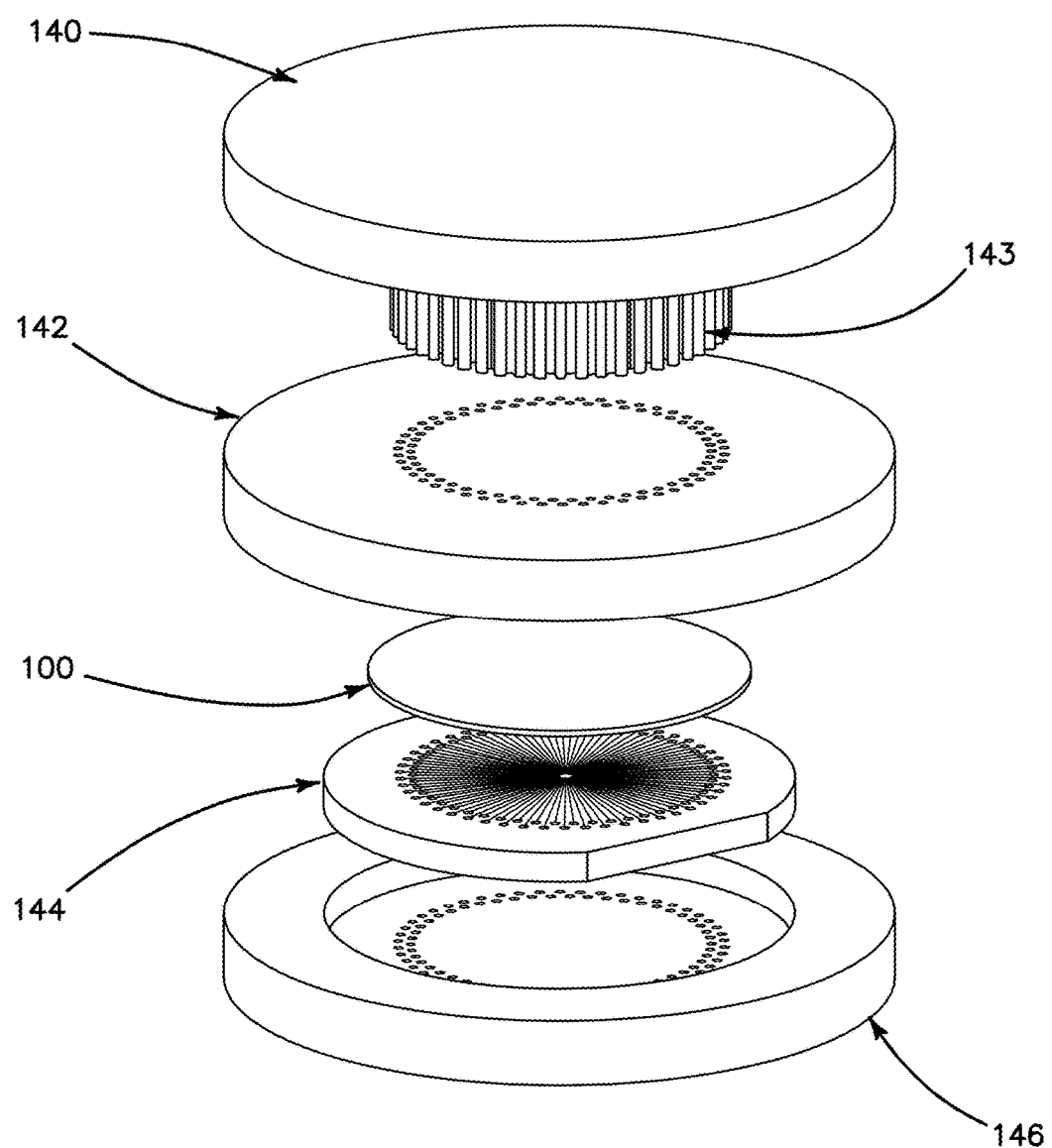
FIG. 5 is a multiplex hole punch.
Figure 5A:
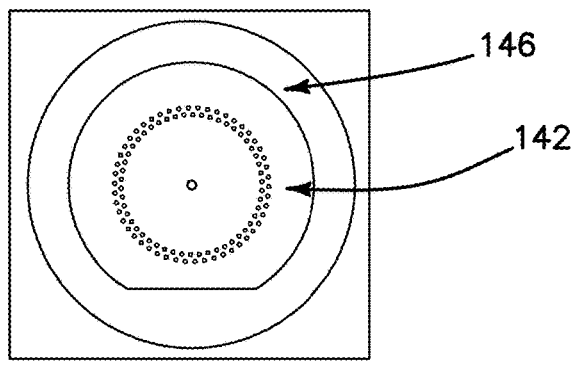
FIG. 5A is an MA Chip top and bottom enclosure assembly.
Figure 5B:
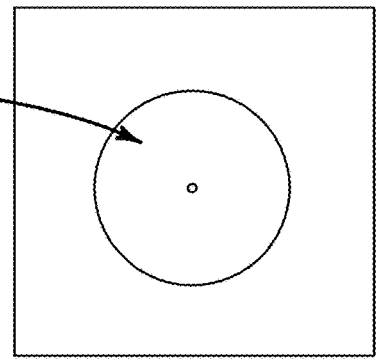
FIG. 5B is an MA Chip with microchannel array.
Figure 5C:
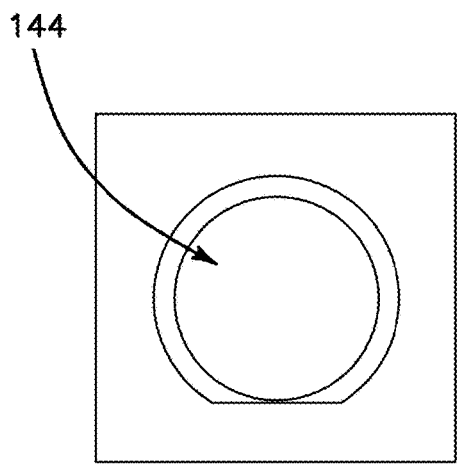
FIG. 5C is a reverse mold of an MA chip.
Figure 5D:
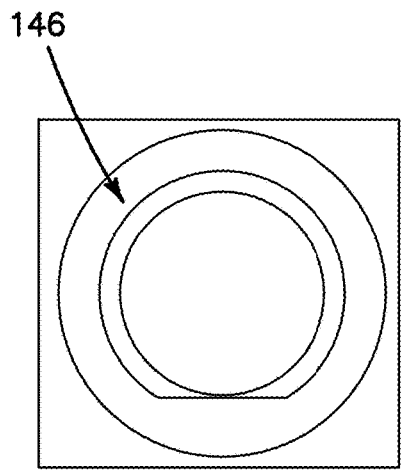
FIG. 5D is an assembled enclosure of an MA chip without the top.
Figure 5E:
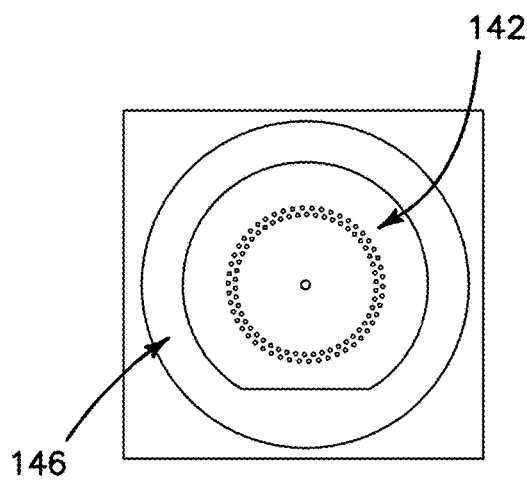
FIG. 5E is a complete assembled enclosure of an MA Chip.
Figure 7:
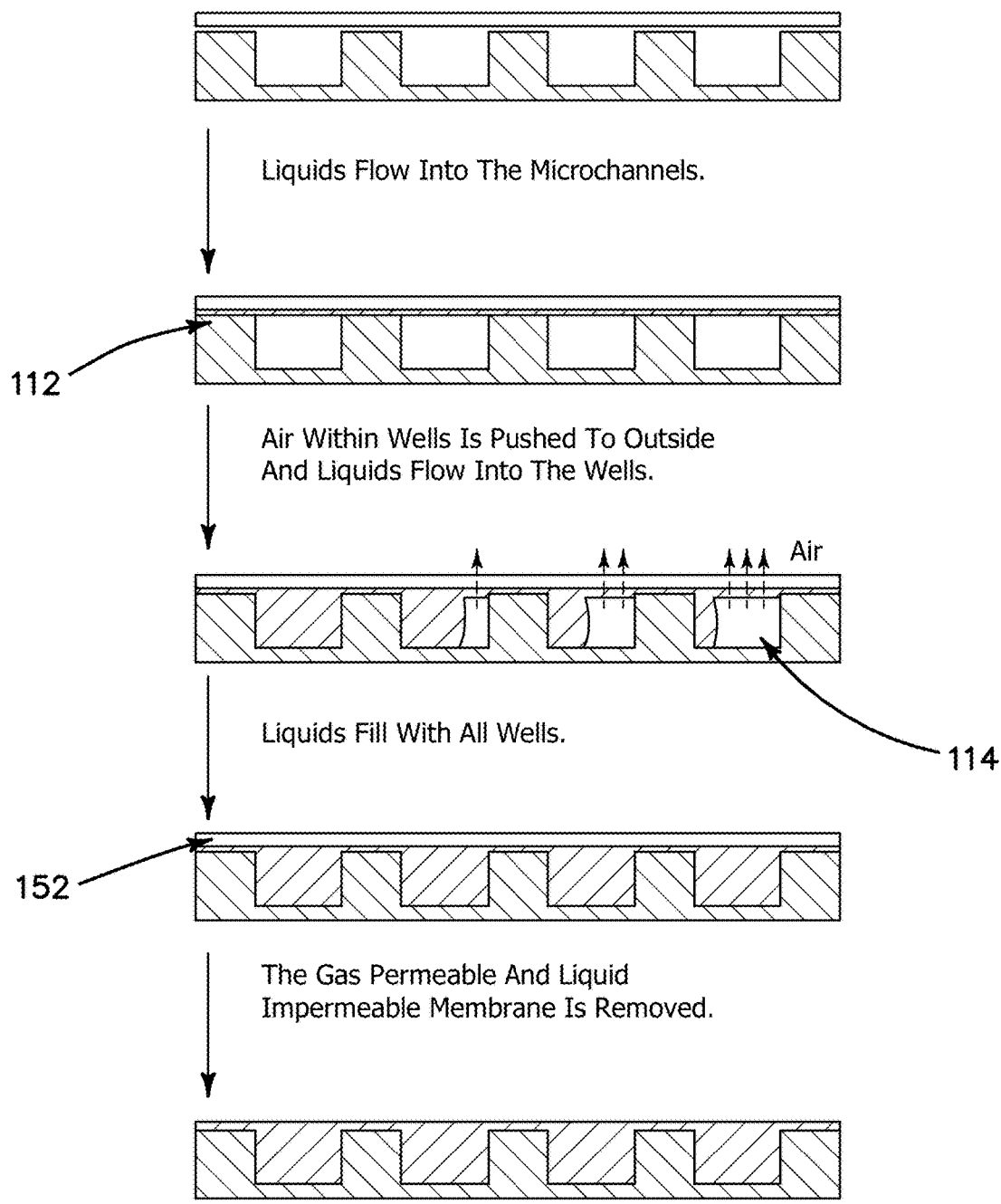
FIG. 7 is a side view diagram of the rMA chip.

In a further variant, referring FIGS. 4C and 4D, a method for making an MA chip 100 is illustrated. The method comprises inserting a first pair of patterned metal injection molds into an injection molding machine. Thermoplastic is injected into the first pair of patterned metal injection molds. Demolding is done to produce an insert 139 having a reverse pattern of the first pair of molds. A second pair of patterned metal injection molds is inserted into the injection molding machine. Thermoplastic is inserted into the second pair of patterned metal injection molds. Demolding is done to produce a base 130 having a reverse pattern of the second pair of molds. A plurality of rivets 134 are inserted on the base 130 into a plurality of rivet through-holes 135 on the insert 139. When the rivets 134 are inserted into the rivet through-holes 135, a center through-hole 137, branched channels, and aliquoting through-holes 131 are sealed and disposed onto the insert 139. FIGS. 4E and 4F illustrate before and after, respectively, the process of assembling the insert 139 and base together 130 as described in the process of FIGS. 4C and 4D. FIG. 4E illustrates a center through-hole 137 which converts into an inlet well 110 in FIG. 4F, an aliquoting through-hole 131 which converts into an outlet well 114 in FIG. 4F, and an open flow channel 133 which converts into a sealed flow channel 129 in FIG. 4F.

In another variant, the branched channel design provides large spacing (>0.4 mm) between the channels. The large space allows a channel-sealing mechanism between the insert 139 and base 130 by inserting rivets 134 into the rivet through-holes 135. The flattened edge 138 is added to ensure the alignment between the MA-Chip insert 139 and base 130. The 24 liquid reservoir wells 132 are designed for carrying buffers, culture mediums, or cell suspension. Each well 132 can contain 30 to 400 μl volume of liquid. The aliquot cells can be transferred to the edge wells for long term culture and cell expansion. The wells can serve as a medium reservoir during on-chip tissue culture to prevent culture medium evaporation. Each well is assigned with an alphabet as a well identification method 136. The well identification alphabets 136 are positively engraved on the top. The patterned bottom surface prevents the viewing area from scratches when it lays down by providing a small gap between the bottom surface and the rough surface. A patterned sink plateau surface 141 exactly matches the MA-Chip insert 139 by using the flattened edge 138 for perfect alignment. The identification numbers for aliquot wells are engraved on the base 130 allowing large spacing between MA-Chip channels. The large spacing between MA-Chip channels provide better manufacturability.

Section 5: Multiplex Hole Puncher Method

In a variant, referring to FIGS. 5, and 5A-5E, a method for creating holes in an MA chip 100 using a multiplex hole puncher, comprises inserting an MA chip 100 between a top 142 and a bottom 146 of an enclosure; aligning the MA chip 100 directly above a reverse mold 144 in the enclosure; inserting a plurality of pins 143 attached to a bottom of a pin head 140 into a plurality of tapered holes on the top 142 of the enclosure; and pressing a top of the pin head 140 so that the MA chip 100 is pushed into the reverse mold 144. The MA chip 100 and enclosure are aligned when the reverse mold 144 has a pattern that matches a pattern on the MA chip 100 and the reverse mold 144 has a flattened edge 138 that matches a flattened edge on the enclosure.

In another variant, the position of the pins 143 is matched with the position of the MA-Chip wells to punch the MA-Chip holes at the same time. This design reduces the hole punching process time. Hollow metal alloy punch pins 143 are secured on the rigid metal alloy substrate such as stainless steel or brass. The metal substrate holds the pins 143 by tapered hole, which allows replacement of the pin 143. The through-holes guide the punch pins 143 to the exact position of the MA-Chip well. The shape of the bottom sink plateau with a flattened edge 138 matches the reverse mold 144 of the MA-Chip 100. The flattened edge 138 is used to align the reverse mold 144 to the top 142 enclosure. The top 142 and bottom 146 enclosures are mirror images. The patterned surface of the reverse mold 144 PDMS block matches the channel and well design of the MA-Chip 100 and thus, ensures the alignment between the MA-Chip holes and channels. The radial shape with a flattened edge 138 matches the sink plateau in the top 142 and bottom 146 enclosures. The flattened edge 138 is used to automatically align the reverse mold 144 to the enclosure.

Section 6: Method of Mass-Producing an MA Chip

In a variant, referring to FIGS. 6A-6F, a method for mass production of MA chips 100, comprises conducting photolithography to produce a silicon mold; injecting Polydimethylsiloxane (PDMS) into the silicon mold; heating the silicon mold containing the PDMS to produce a first layer of an MA chip 100 having channels and an inlet well 110; cutting plastic material with a laser to produce a second layer of an MA chip 100 having a well array and channels; and aligning the first layer directly on top of the second layer so the channels on both layers overlap. The channels on the first layer are longer and narrower than the channels on the second layer.

In another variant, a method for mass production of MA chips 100, comprises cutting plastic material with a laser to produce a first layer of an MA chip 100 having a well array and an inlet well 110; conducting photolithography to produce a silicon mold; injecting Polydimethylsiloxane (PDMS) into the silicon mold; heating the silicon mold containing the PDMS to produce a second layer of an MA chip 100 having radial channels and an alignment mark array; and aligning the first layer directly on top of the second layer so the well array and the alignment mark array overlap.

In a further variant, the assembled MA-Chip 100 is made of two patterned layers. The top layer is made of PDMS by photolithography and contains long and narrow channels (2-4 cm in length and 0.03-0.1 mm in width) and a central through-hole (2-4 mm in diameter). The bottom layer is made of plastic materials by laser cutting or injection molding, such as PS, PP, PMMA, and PC, and contains a well array (1-2 mm in diameter) and associated short and wide channels (0.5-2.5 mm in length and 0.3-0.5 mm in width). When the two patterned layers are assembled and bonded, the long and narrow channels and short and wide channels can be well overlapped for uniform liquid distribution. A microliter of liquid, typically between 100 µL and 200 µL, can be injected into the inlet well 110 by a pipette and uniformly dispensed into 100 open wells.

Section 7: Rectangular MA Chip

Figure 8:
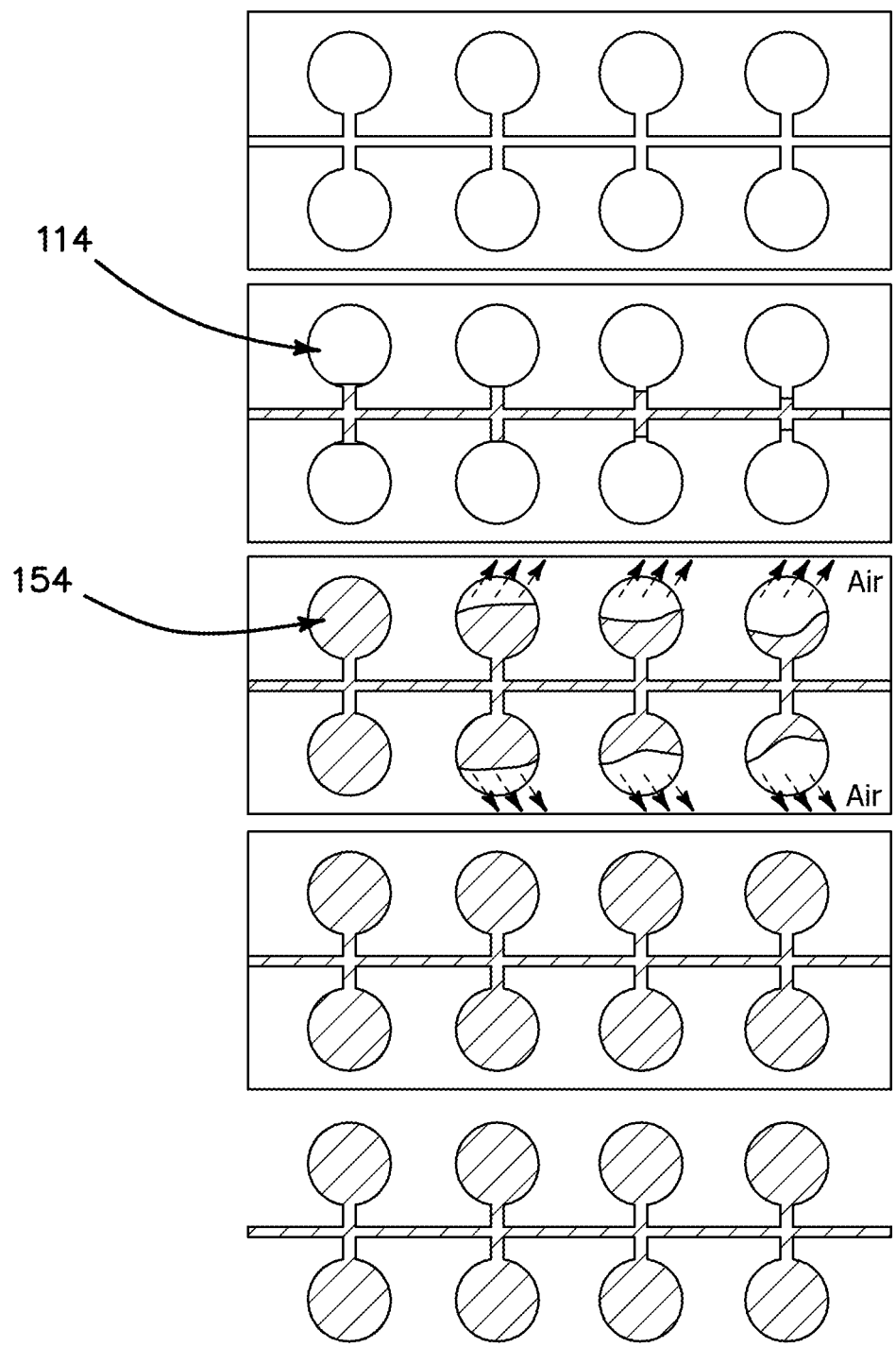
FIG. 8 is a top view diagram of the rMA chip.
Figure 8A:
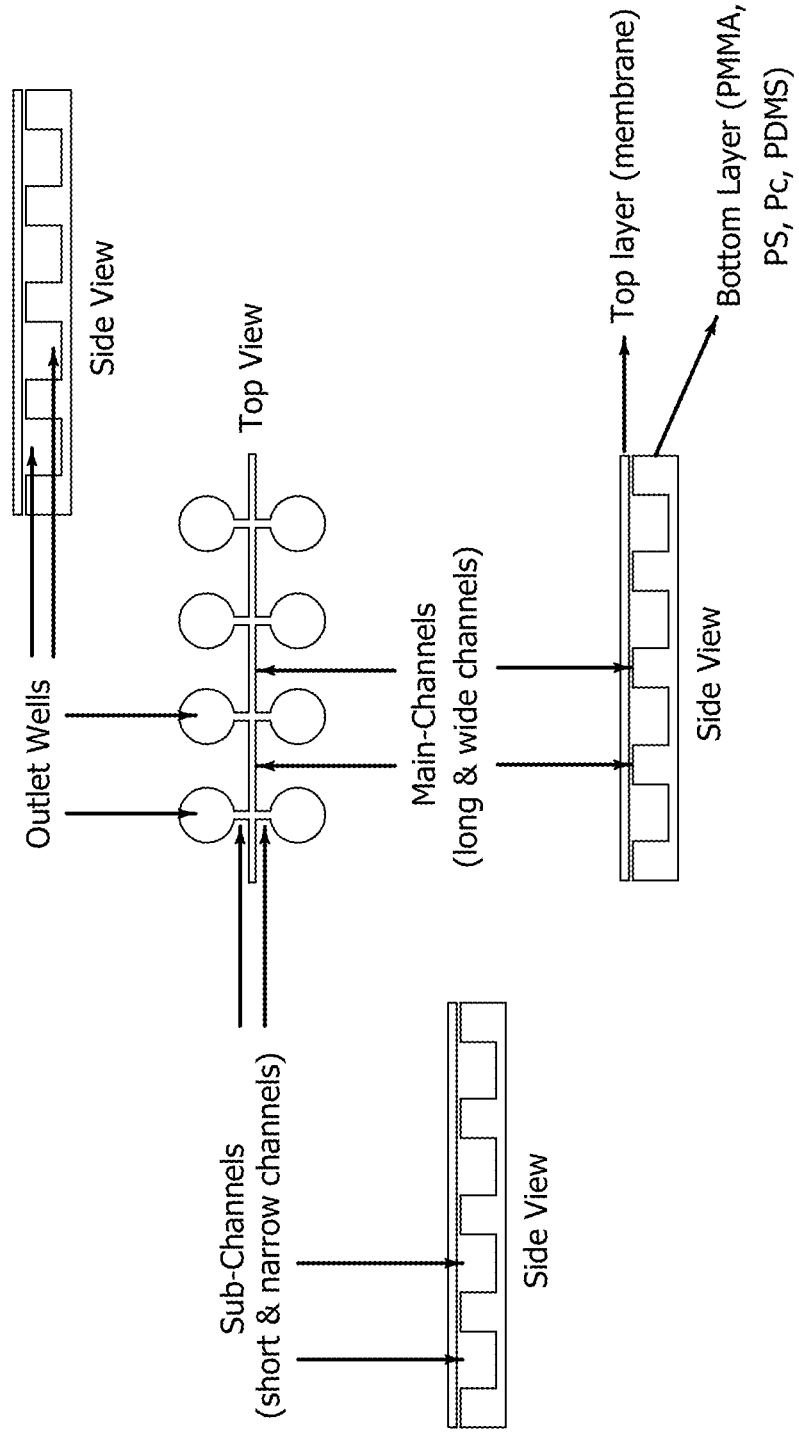
FIG. 8A is a method of assembling the rMA chip.
Figure 10B:
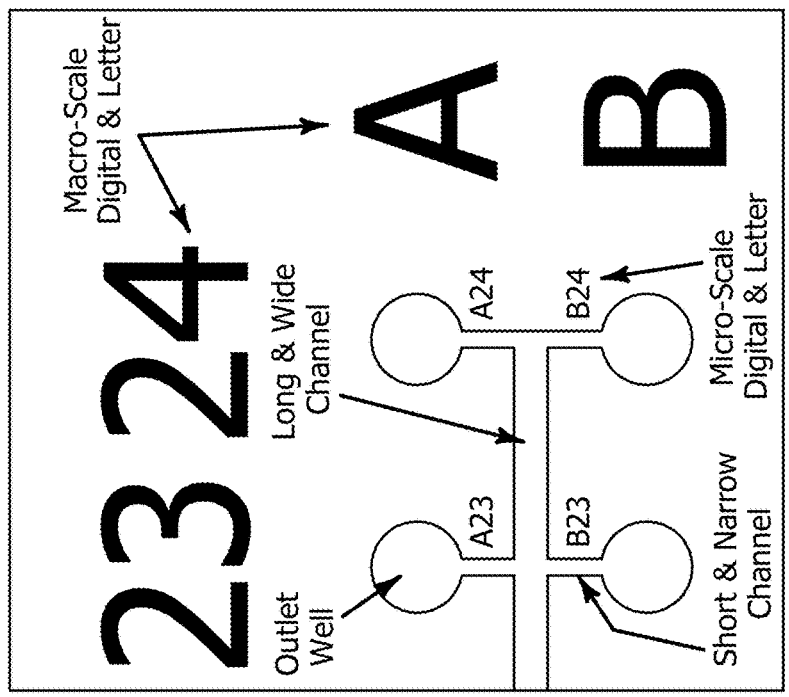
FIG. 10B is a magnified portion of an rMA chip.
Figure 10A:
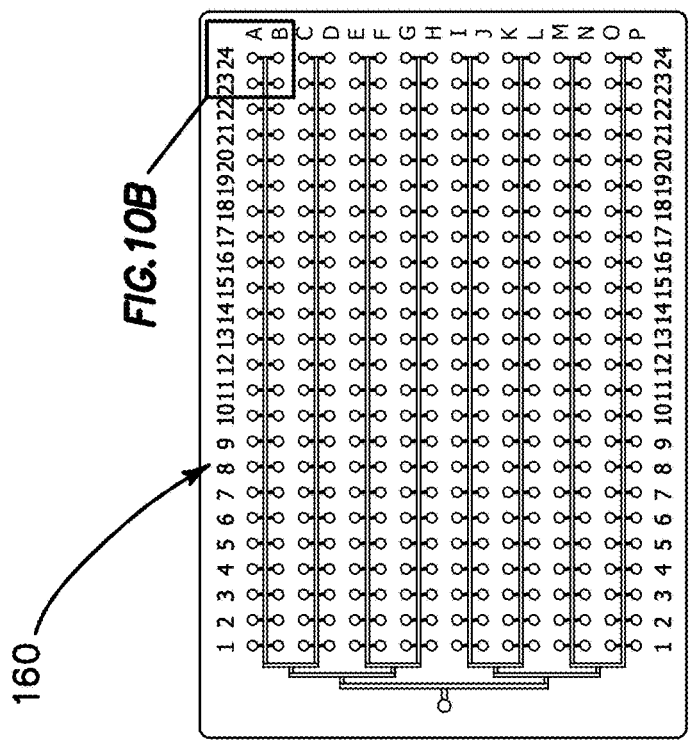
FIG. 10A is a design of an rMA chip.
Figure 10C:
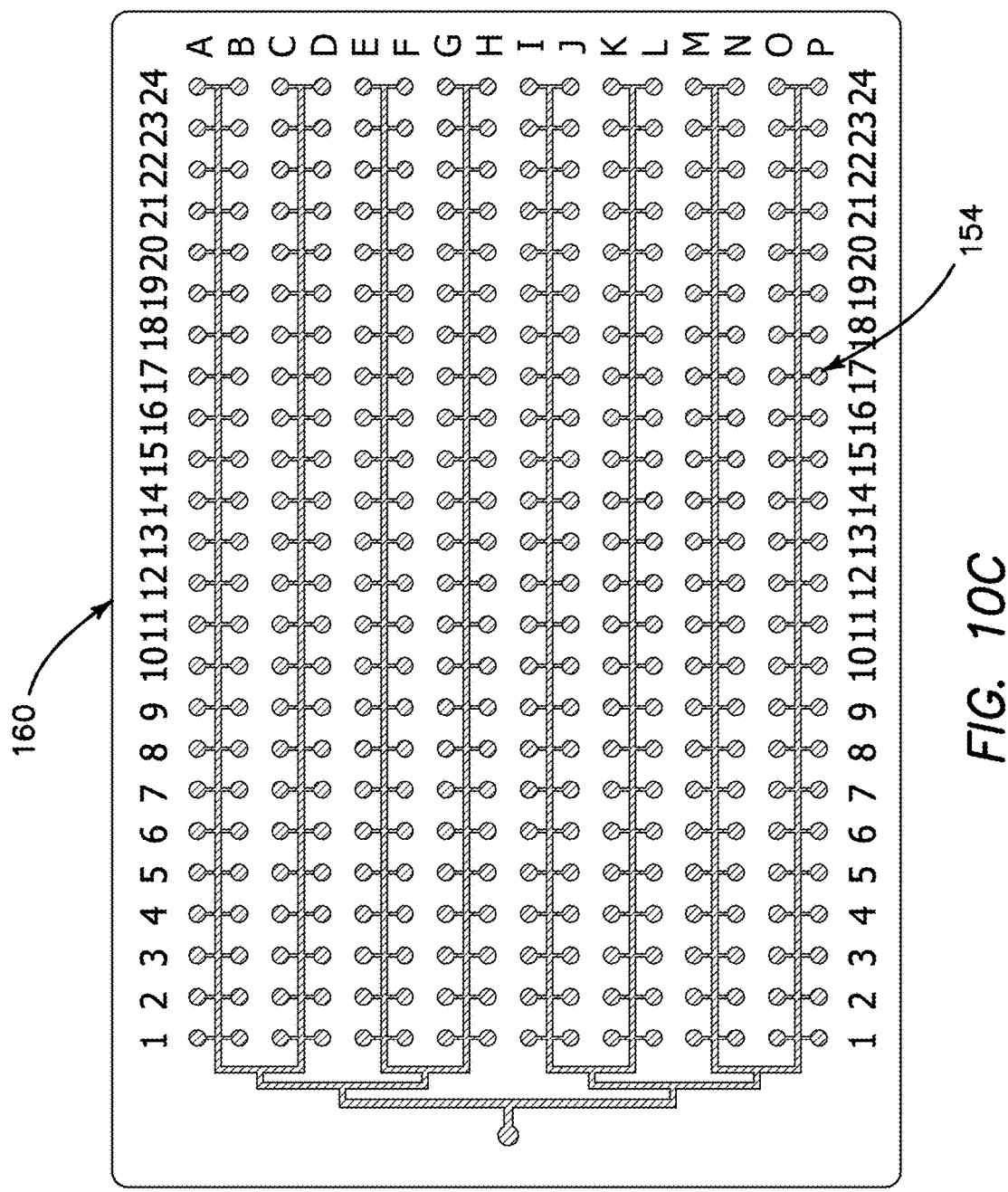
FIG. 10C is a prototype of a PMMA rMA chip.

In a variant, referring to FIGS. 7-10C, a method for making MA chips 100, comprises cutting plastic material with a laser to produce a first layer of an MA chip 100 having an inlet well 110, outlet well array, main-channel array, and sub-channel array; adhering a second membrane layer 152 on top of the first layer using an adhesive on the second membrane layer 152; cutting an area of the membrane 152 directly on top of the inlet well 110 with a puncher; and securing a PDMS cap on top of the exposed inlet well 110. The cap is configured to receive liquid, which distributes from the cap to the inlet well 110, the main channels, the sub-channels, and finally the outlet wells 114, as illustrated in FIG. 8A.

In another variant, a rectangular MA-Chip (rMA-Chip) 156 where all outlet wells 114 are patterned in a rectangular array. The top of the well array is connected to the channel array and both of them are sealed by a gas-permeable and liquid-impermeable membrane 152. Liquids are loaded with pipettes or syringes and will flow into the channel array and then into the well array by continuously pushing the air to the outside. After loading the liquid, the membrane 152 is removed and the well array with liquid 154 inside is obtained. After removing the membrane 152, the wells are open to the air and the liquids associated with single cells may be confirmed by microscope and then retrieved with a pipette.

In a further variant, the rMA-Chip 156 is rectangular in shape and 127.8±5 mm in length, 85.5±3 mm in width, and 1-10 mm in height. The rMA-Chip 156 has two layers: the top layer and the bottom layer. The top layer is a membrane 152 with a thickness of 0.03-0.3 mm. The top layer is gas-permeable and liquid-impermeable. The top layer is biocompatible and not harmful to cells. The top layer is transparent and flexible.

In yet another variant, the outlet wells 114 are 0.5-5 mm in diameter and 1-10 mm in height. The number of outlet wells 114 in one rMA-Chip can be 32, 64 (32×2), 96 (32×4), 384 (96×4) 160, or 1536 (384×4). Outlet wells 114 can be in other shapes such as a rectangle, triangle, or oval. Outlet wells 114 are uniformly distributed throughout the rMA-Chip 156. Each outlet well 114 is labeled by a micro-scale number and letter designed for microscopic observation and macro-scale number and letter designed for naked-eye observation.

What is claimed is:

1. A microfluidic aliquot (MA) chip for isolating cells, comprising:
   a chip having a center, a top surface, a bottom surface, an outer edge and a thickness;
   an inlet well disposed substantially at the center of the chip, extending into and accessible from the top surface of the chip;
   a plurality of outlet wells disposed in an outer portion of the chip, extending into and accessible from the top surface of the chip;
   a plurality of multiple segments that extend from the inlet well to the outlet wells, wherein each outlet well is disposed at the end of each of the plurality of multiple segments;
   wherein the multiple segments comprise branched channels;
   wherein the chip is configured to maintain uniform distribution of a liquid and cells from the inlet well to the outlet wells; and
   wherein every other outlet well is disposed farther away from the inlet well than an adjacent outlet well.

2. The MA chip of claim 1, wherein the chip comprises:
   a plurality of first segments that form an inner section, a plurality of last segments that form an outer section, and a plurality of segments between the first segments and the last segments that form a middle section;
   wherein the first segment is connected to the center inlet well in a radial pattern;
   wherein each segment after the first segment is divided from a prior segment in a radial pattern; wherein a first channel of a last segment is shorter than a second channel of the last segment.

3. The MA chip of claim 2, wherein a plurality of segments in the middle section form a curved portion generally in the shape of a bend, whereby one of the first segments is joined to the bend of a segment in the middle section.

4. The MA chip of claim 1, wherein the chip comprises:
   four first segments that extend outward from the inlet well in four cardinal directions, respectively;
   wherein each segment branches at a 90 degree angle in two opposite directions into another segment forming a set of branched channels; and
   wherein each set of branched channels on a last segment correspond to a set of outlet wells.

5. The MA chip of claim 1, wherein the chip comprises:
   a plurality of first segments that extend outward radially from the inlet well;
   wherein each segment branches at a 90 degree angle in two opposite directions into another segment forming a set of branched channels; and
   wherein each set of branched channels on a last segment correspond to a set of outlet wells.

6. The MA chip of claim 1, wherein the chip comprises:
   a sheet of material selected from a group consisting of polydimethylsiloxane (PDMS), PMMA (poly(methyl methacrylate)), PS (polystyrene), and PC (polycarbonate);
   wherein the sheet has a top surface and a bottom surface, that correspond to the top and bottom surfaces of the chip, respectively.

7. The MA chip of claim 1, wherein the chip comprises:
a center inlet well having a diameter of 2-4 mm and a volume of 3-5 µl;
a plurality of side outlet wells having a diameter of 1.5-2 mm and a volume of 1-3 µl;
a plurality of branched channels having a width of 50-100 µm; and
wherein the chip is configured to fit within a Petri dish of 8.5-10 cm.

8. The MA chip of claim 1, wherein the chip comprises:
a first layer having a top surface and a bottom surface;
a second membrane layer having a top surface and a bottom surface;
wherein the bottom surface of the second membrane layer has an adhesive; and
wherein the bottom surface of the second membrane layer is configured to adhere to the top surface of the first layer.

9. The MA chip of claim 8, wherein the top surface of the first layer comprises:
an inlet well;
an outlet well array;
a main-channel array;
a sub-channel array;
wherein the main channels are longer and wider than the sub-channels;
wherein the main channels extend outward from the inlet well to the sub-channels; and
wherein the sub-channels extend from the main channels to the outlet wells.

10. The MA chip of claim 8, wherein the chip comprises:
a second membrane layer having a thickness of 0.03-0.3 mm;
a plurality of outlet wells having a diameter of 0.5-5 mm and a height of 1-10 mm; and
wherein the chip has a length of 127.8±5 mm, a width of 85.5±3 mm, and a height of 1-10 mm.

11. The MA chip of claim 1, wherein the inlet well comprises a cap having a hole that is configured to attach onto the inlet well and receive a cell suspension.

12. The MA chip of claim 1, wherein the center inlet well is configured to receive and distribute liquid through the branched channels and into the outlet wells.

* * * * *